(12) United States Patent
Onuma

(10) Patent No.: US 10,018,589 B2
(45) Date of Patent: Jul. 10, 2018

(54) ANALYSIS METHOD AND ANALYSIS SYSTEM

(71) Applicant: ARKRAY, Inc., Kyoto-shi (JP)

(72) Inventor: Naotsugu Onuma, Kyoto (JP)

(73) Assignee: ARKRAY, Inc., Kyoto-shi, Kyoto (JP)

( * ) Notice: Subject to any disclaimer, the term of this patent is extended or adjusted under 35 U.S.C. 154(b) by 121 days.

(21) Appl. No.: 14/846,097

(22) Filed: Sep. 4, 2015

(65) Prior Publication Data

US 2016/0069835 A1 Mar. 10, 2016

(30) Foreign Application Priority Data

Sep. 4, 2014 (JP) ................................. 2014-180138
Aug. 4, 2015 (JP) ................................. 2015-153971

(51) Int. Cl.
  *G01N 27/447* (2006.01)
  *G01N 1/40* (2006.01)
  *G01N 33/72* (2006.01)

(52) U.S. Cl.
  CPC ..... *G01N 27/44704* (2013.01); *G01N 1/4077* (2013.01); *G01N 27/44769* (2013.01); *G01N 33/721* (2013.01); *G01N 27/44721* (2013.01); *G01N 2001/4088* (2013.01); *G01N 2333/805* (2013.01)

(58) Field of Classification Search
  CPC ....... G01N 27/44704; G01N 27/44769; G01N 33/721; G01N 1/4077; G01N 1/44769; G01N 2333/805
  See application file for complete search history.

(56) References Cited

U.S. PATENT DOCUMENTS

| | | |
|---|---|---|
| 5,599,433 A | 2/1997 | Keo et al. |
| 7,887,686 B2 | 2/2011 | Robert et al. |
| 8,361,292 B2 | 1/2013 | Nakayama et al. |

(Continued)

FOREIGN PATENT DOCUMENTS

| | | |
|---|---|---|
| CN | 102077085 A | 5/2011 |
| CN | 102128873 A | 7/2011 |

(Continued)

OTHER PUBLICATIONS

Extended European Search Report dated Feb. 9, 2016 in corresponding EP Application No. 15182811.8.

(Continued)

*Primary Examiner* — Jayne L Mershon
(74) *Attorney, Agent, or Firm* — Knobbe, Martens, Olson & Bear, LLP

(57) ABSTRACT

A method for analyzing a sample using capillary electrophoresis is provided. By the method, following steps are performed. First, an original sample and an anionic group-containing compound are fixed to form a mixed sample, where the original sample contains an analysis component to be analyzed and a sub component other than the analysis component. Then, an aggregate of the sub component and the anionic group-containing compound is removed from the mixed sample. Then, electrophoresis is performed in a capillary tube with respect to a complex in which the analysis component and the anionic group-containing compound are bound to each other, while the mixed sample is continuously supplied.

17 Claims, 6 Drawing Sheets

(56) References Cited

U.S. PATENT DOCUMENTS

| | | | |
|---|---|---|---|
| 2004/0146849 A1* | 7/2004 | Huang | B01L 3/502761 435/4 |
| 2008/0003678 A1 | 1/2008 | Hattori et al. | |
| 2010/0116660 A1 | 5/2010 | Tanaka et al. | |
| 2010/0181199 A1 | 7/2010 | Sugiyama et al. | |
| 2010/0258440 A1 | 10/2010 | Sugiyama et al. | |
| 2011/0174621 A1 | 7/2011 | Yonehara et al. | |
| 2016/0041153 A1* | 2/2016 | Brown | G01N 33/5308 435/7.23 |

FOREIGN PATENT DOCUMENTS

| | | |
|---|---|---|
| EP | 2060912 A1 | 5/2009 |
| EP | 2757368 A1 | 7/2014 |
| JP | 1997-510792 A | 10/1997 |
| JP | 2006-145537 A | 6/2006 |
| JP | 2009-109230 A | 5/2009 |
| WO | 2008/136321 A1 | 11/2008 |
| WO | 2008/136465 A8 | 11/2008 |
| WO | 2010/010859 A1 | 1/2010 |

OTHER PUBLICATIONS

Office Action issued in Chinese Patent Application No. 201510548712.1 dated Aug. 18, 2017.
Non-Final Office Action issued in connection with U.S. Appl. No. 15/686,016 dated Apr. 9, 2018.

* cited by examiner

ANALYSIS METHOD AND ANALYSIS SYSTEM

BACKGROUND OF THE INVENTION

1. Field of the Invention

The present invention relates to an analysis method and an analysis system.

2. Description of Related Art

As an indicator indicating a state of a living body, glycation degrees of various proteins are analyzed. Of these, a glycation degree of hemoglobin (Hb) in blood cells, in particular, stable HbA1c (hereinafter, may be referred to as "s-HbA1c" in an abridged manner) is regarded as an important indicator in diagnosis, treatment, and the like of diabetes because it reflects a history of previous blood glucose levels in a living body. HbA1C is hemoglobin that is glycated at the N-terminal valine of the β-chain of HbA (α2β2).

Examples of a method for analyzing Hb such as s-HbA1c include electrophoresis methods. JP-A-2006-145537, JP-A-H9-510792, WO 2010/010859, JP-A-2009-109230, and WO 2008/136321 have disclosed to, in order to properly perform analysis and improve the precision, add an additional component to an electrophoretic liquid. In particular, JP-A-2009-109230 and WO 2008/136321 have disclosed chondroitin sulfate as an example of an additional component to an electrophoretic liquid. Furthermore, WO 2008/136465 describes an analysis method that continuously supplies a sample also during separation of the sample by electrophoresis, in order to reduce the size of a chip for use in an analysis using an electrophoresis method.

Blood, which is a typical example of a sample, is a sample derived from a living body. Accordingly, for example, if blood collected from a patient is used as a sample, the collected blood may have various properties depending on the disease state, the physical make-up, and the like of the patient. It is desirable to perform accurate analysis whatever properties blood used as a sample has. However, at present, how the additional components or the specific configuration of the analysis methods described above may inhibit the analysis has hardly been identified. The same is applied to samples other than blood.

SUMMARY OF THE INVENTION

The present invention has been proposed under the above circumstances, and it is an object thereof to provide an analysis method and an analysis system capable of improving the analysis precision.

A first aspect of the present invention is directed to a method for analyzing a sample using a capillary electrophoresis method, including: a step of mixing an original sample and an anionic group-containing compound, thereby forming a mixed sample, the original sample containing an analysis component to be analyzed and a sub component other than the analysis component; a step of removing an aggregate of the sub component and the anionic group-containing compound from the mixed sample; and a step of performing electrophoresis in a capillary tube where the electrophoresis is performed with a complex in which the analysis component and the anionic group-containing compound are bound to each other, in a state where the mixed sample is continuously supplied.

In a preferable embodiment, in the removing step, the aggregate is removed by filtering.

In a preferable embodiment, in the removing step, the aggregate is removed by centrifugal separation.

In a preferable embodiment, the anionic group-containing compound is an anionic group-containing polysaccharide.

In a preferable embodiment, the anionic group-containing polysaccharide is at least one polysaccharide selected from the group consisting of sulfated polysaccharide, carboxylated polysaccharide, sulfonated polysaccharide, and phosphorylated polysaccharide.

In a preferable embodiment, the sulfated polysaccharide is chondroitin sulfate.

In a preferable embodiment, the analysis component is hemoglobin.

In a preferable embodiment, the sub component is a lipid.

A second aspect of the present invention is directed to a system for analyzing a sample using a capillary electrophoresis method, where the system includes: a mixing portion that mixes an original sample and an anionic group-containing compound, thereby forming a mixed sample, the original sample containing an analysis component to be analyzed and a sub component other than the analysis component; a removing portion that removes an aggregate of the sub component and the anionic group-containing compound from the mixed sample; and an analysis portion that has a capillary tube, and performs electrophores is in the capillary tube with a complex in which the analysis component and the anionic group-containing compound are bound to each other, in a state where the mixed sample is continuously supplied.

In a preferable embodiment, the removing portion has a filter.

In a preferable embodiment, the system is further provided with a disposable analysis chip including the capillary tube, an introducing tank linked to one end of the capillary tube, and a discharging tank linked to the other end of the capillary tube, where the filter is provided on an introduction path to the introducing tank of the analysis chip.

In a preferable embodiment, the mixing portion is a mixing tank formed in the analysis chip.

In a preferable embodiment, the removing portion has a centrifugal separator.

According to the present invention, an aggregate of the sub component and the anionic group-containing compound is removed. Thus, when electrophoresis is performed in the capillary tube in a state where the mixed sample is continuously supplied, noise in the measurement results can be suppressed, and, thus, the analysis precision can be improved.

Other features and advantages of the present invention will become more apparent from the detailed description given below with reference to the attached drawings.

DESCRIPTION OF THE PREFERRED EMBODIMENTS

Hereinafter, preferred embodiments of the present invention will be specifically described with reference to the drawings.

Figure 1:
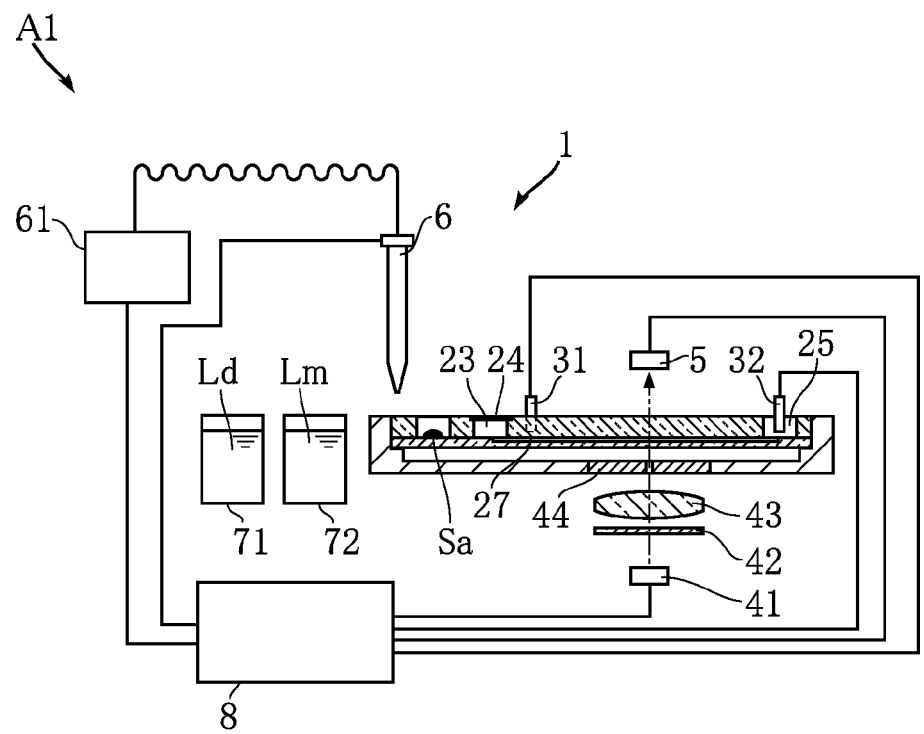
FIG. 1 is a schematic system view showing an analysis system according to a first embodiment of the present invention.

FIG. 1 shows an analysis system according to the first embodiment of the present invention. An analysis system A1 of this embodiment includes an analysis device 1 and an analysis chip 2. The analysis system A1 is a system that carries out an analysis method on a sample Sa using an electrophoresis method. Although there is no particular limitation on the sample Sa, in this embodiment, a description will be given using blood collected from a human body as an example. Of the components contained in the sample Sa, a component that is to be analyzed is defined as an analysis component.

Examples of the analysis component include hemoglobin (Hb), albumin (Alb), globulin ($\alpha 1$, $\alpha 2$, $\beta$, $\gamma$ globulin), fibrinogen, and the like. Examples of the hemoglobin include normal hemoglobin (HbA0), glycated hemoglobin, modified hemoglobin, fetal hemoglobin (HbF), and the like. Examples of the glycated hemoglobin include hemoglobin A1a (HbA1a), hemoglobin A1b (HbA1b), hemoglobin A1c (HbA1c), GHbLys, and the like. Examples of the hemoglobin A1c include stable HbA1C (s-HbA1c), unstable HbA1c, and the like. Examples of the modified hemoglobin include carbamylated Hb, acetylated Hb, and the like. In the description below, a case in which the analysis component is stable HbA1c (s-HbA1c) will be described as an example. Typically, s-HbA1c is used as an indicator in diagnosis, treatment, and the like of diabetes.

Figure 2:
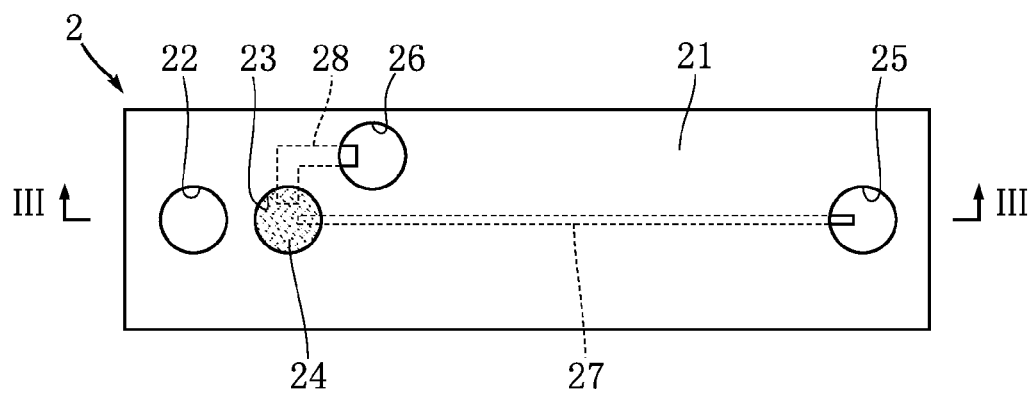
FIG. 2 is a plan view showing an analysis chip for use in the analysis system in FIG. 1.
Figure 3:
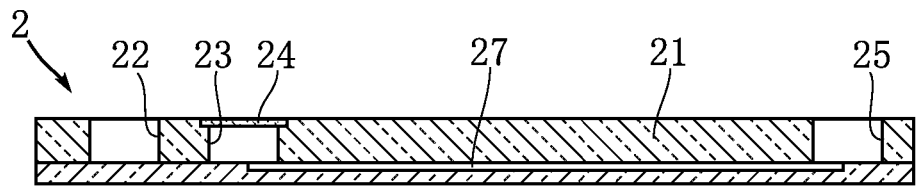
FIG. 3 is a cross-sectional view taken along the line III-III in FIG. 2.

The analysis chip 2 enables an analysis to be performed on the sample Sa in a state where the analysis chip 2 holding the sample Sa is set in the analysis device 1. In this embodiment, the analysis chip 2 is configured as a so-called disposable analysis chip that is intended to be disposed of after an analysis is performed once or a designated number of times. As shown in FIGS. 2 and 3, the analysis chip 2 includes a main body 21, a mixing tank 22, an introducing tank 23, a filter 24, a discharging tank 25, an electrode tank 26, a capillary tube 27, and a communication flow path 28. FIG. 2 is a plan view of the analysis chip 2, and FIG. 3 is a cross-sectional view taken along the line III-III in FIG. 2.

The main body 21 is a base for the analysis chip 2. There is no particular limitation on the material of the main body 21, and examples thereof include glass, molten silica, plastic, and the like. In this embodiment, the main body 21 has a configuration in which an upper portion and a lower portion in FIG. 3 are bonded to each other, but the main body 21 may be formed in one piece.

The mixing tank 22 is an example of a mixing portion that performs a mixing step (described later) of mixing the sample Sa and a diluting liquid Ld. The mixing tank 22 is formed, for example, as a through-hole that is formed through the upper portion of the main body 21. The introducing tank 23 is a tank to which a mixed sample Sm obtained by the mixing step in the mixing tank 22 is to be introduced. The introducing tank 23 is formed, for example, as a through-hole that is formed through the upper portion of the main body 21.

The filter 24 is provided at an opening portion of the introducing tank 23 (i.e., an example of an introduction path to the introducing tank 23), and is an example of a removing portion (filtering means) in the present invention. There is no limitation on the specific configuration of the filter 24, as long as a removing step (described later) is properly performed, and preferable examples thereof include a cellulose acetate membrane filter (manufactured by ADVANTEC, pore size 0.45 μm).

The discharging tank 25 is a tank that is positioned downstream of an electroosmotic flow in the electrophoresis method. The discharging tank 25 is formed, for example, as a through-hole that is formed through the upper portion of the main body 21. The electrode tank 26 is a tank into which an electrode 31 is to be inserted in an analysis step in the electrophoresis method. The electrode tank 26 is formed, for example, as a through-hole that is formed through the upper portion of the main body 21. The communication flow path 28 links the introducing tank 23 and the electrode tank 26, and forms a communication path between the introducing tank 23 and the electrode tank 26.

The capillary tube 27 links the introducing tank 23 and the discharging tank 25, and an electroosmotic flow in the electrophoresis method is generated in this capillary tube 27. The capillary tube 27 is formed, for example, as a groove that is formed in the lower portion of the main body 21. Note that, in the main body 21, a recess portion and the like may be formed for facilitating irradiation of the capillary tube 27 with light and emission of light that has been transmitted through the capillary tube 27. There is no particular limitation on the size of the capillary tube 27, but, for example, the width is 25 μm to 100 μm, the depth is 25 μm to 100 μm, and the length is 5 mm to 150 mm. The size of the entire analysis chip 2 is set as appropriate according to the size of the capillary tube 27, the size and the arrangement of the mixing tank 22, the introducing tank 23, the discharging tank 25, and the electrode tank 26, and the like.

The analysis device 1 analyzes the sample Sa in a state where the analysis chip 2 to which the sample Sa was added dropwise is set in the analysis device 1. The analysis device 1 includes electrodes 31 and 32, a light source 41, an optical filter 42, a lens 43, a slit 44, a detector 5, an injector 6, a pump 61, a diluting liquid tank 71, an electrophoretic liquid tank 72, and a control portion 8.

The electrode 31 and the electrode 32 are for applying a predetermined voltage to the capillary tube 27 in the electrophoresis method. The electrode 31 is inserted into the electrode tank 26 of the analysis chip 2, and the electrode 32 is inserted into the discharging tank 25 of the analysis chip 2. There is no particular limitation on a voltage applied to the electrode 31 and the electrode 32, and examples thereof include a range of 0.5 kV to 20 kV.

The light source 41 is a portion that emits light for light absorbance measurement in the electrophoresis method. The light source 41 includes, for example, an LED chip that emits light in a predetermined wavelength range. The optical filter 42 is for attenuating light having a predetermined wavelength, of the light from the light source 41, while allowing light having the other wavelengths to be transmitted therethrough. The lens 43 is for converging light that has been transmitted through the optical filter 42, on an analysis point of the capillary tube 27 of the analysis chip 2. The slit 44 is for removing unnecessary light that may cause scattering or the like, of the light that has been converged by the optical filter 42.

The detector 5 is for receiving light that has been transmitted through the capillary tube 27 of the analysis chip 2, and includes, for example, a photodiode, a photo IC, or the like.

The injector 6 is for injecting a desired amount of diluting liquid Ld, electrophoretic liquid Lm, or mixed sample Sm, and includes, for example, a nozzle. The injector 6 can be freely moved between a plurality of predetermined positions in the analysis device 1 by an unshown drive mechanism. The pump 61 functions as a suction source and an ejection source into and from the injector 6. Furthermore, the pump 61 may be used as a suction source and an ejection source into and from unshown ports provided in the analysis device 1. The ports are used for filling an electrophoretic liquid Lm and the like. Note that a dedicated pump other than the pump 61 may be provided.

The diluting liquid tank 71 is a tank for storing the diluting liquid Ld. The diluting liquid tank 71 may be a tank permanently installed in the analysis device 1, or may be a container set in the analysis device 1 in a state of containing a predetermined amount of diluting liquid Ld. The electrophoretic liquid tank 72 is a tank for storing the electrophoretic liquid Lm. The electrophoretic liquid tank 72 may be a tank permanently installed in the analysis device 1, or may be a container set in the analysis device 1 in a state of containing a predetermined amount of electrophoretic liquid Lm.

The diluting liquid Ld is mixed with the sample Sa to form a mixed sample Sm. There is no particular limitation on the main component of the diluting liquid Ld. Examples thereof include water and physiological saline, and preferable examples thereof include a liquid having components similar to those of the electrophoretic liquid Lm (described later). The diluting liquid Ld is obtained by adding an anionic group-containing compound to the main component. Examples of the anionic group-containing compound include an anionic group-containing polysaccharide. The anionic group-containing polysaccharide is, for example, at least one polysaccharide selected from the group consisting of sulfated polysaccharides, carboxylated polysaccharides, sulfonated polysaccharides, and phosphorylated polysaccharides. The carboxylated polysaccharide is preferably alginic acid or a salt thereof (e.g., sodium alginate). The sulfated polysaccharide is, for example, chondroitin sulfate. There are seven types of chondroitin sulfates A, B, C, D, E, H, and K and any of them may be used. In the description below, a case in which the diluting liquid Ld is obtained by adding chondroitin sulfate to the main component that is the same as the electrophoretic liquid Lm will be described as an example. The anionic group-containing compound (chondroitin sulfate) has a concentration of, for example, 0.01 to 5% by weight.

The electrophoretic liquid Lm is a medium with which the discharging tank 25 and the capillary tube 27 are filled, and in which an electroosmotic flow in the electrophoresis method is generated, in the analysis step in the electrophoresis method. There is no particular limitation on the electrophoretic liquid Lm, but preferable examples thereof include those using an acid. Examples of the acid include citric acid, maleic acid, tartaric acid, succinic acid, fumaric acid, phthalic acid, malonic acid, and malic acid. The electrophoretic liquid Lm preferably contains a weak base. Examples of the weak base include arginine, lysine, histidine, tris, and the like. The electrophoretic liquid Lm has a pH of, for example, 4.5 to 6. Examples of the buffer type of the electrophoretic liquid Lm include MES, ADA, ACES, BES, MOPS, TES, HEPES, and the like. The anionic group-containing compound as in the description of the diluting liquid Ld is added also to the electrophoretic liquid Lm. The anionic group-containing compound (chondroitin sulfate) has a concentration of, for example, 0.01 to 5% by weight.

The control portion 8 controls various portions in the analysis device 1. The control portion 8 includes, for example, a CPU, a memory, an interface, and the like.

Figure 4:
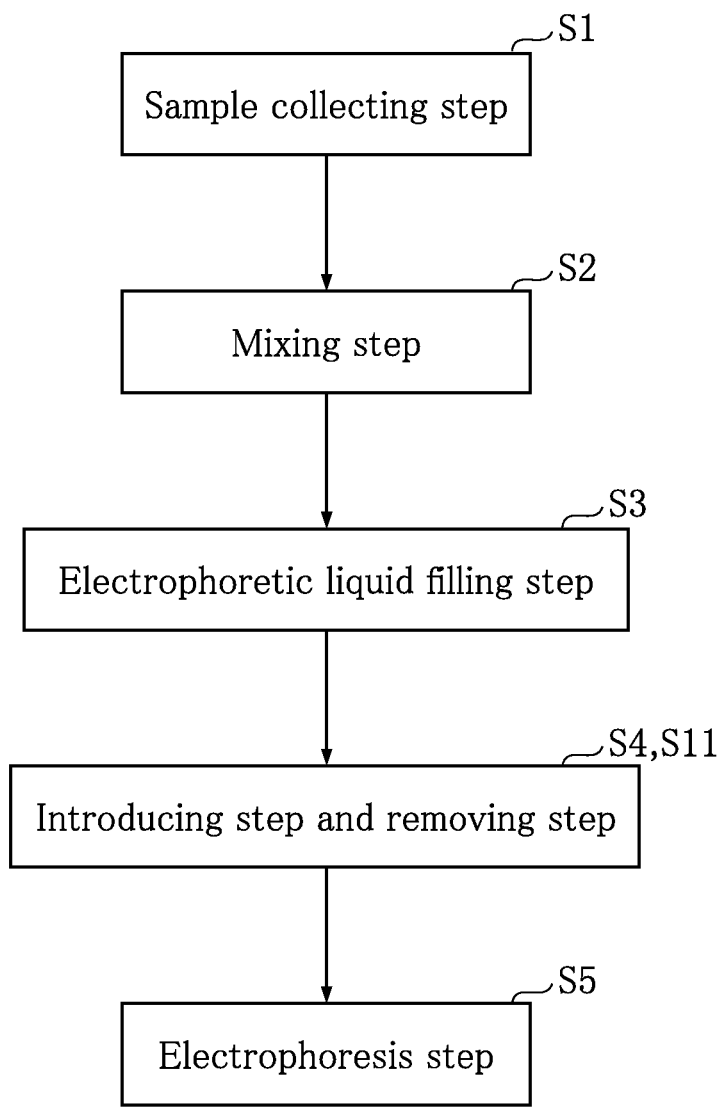
FIG. 4 is a flowchart showing an analysis method according to the first embodiment of the present invention.

Next, the analysis method according to the first embodiment of the present invention using the analysis system A1 will be described below. FIG. 4 is a flowchart showing an analysis method of this embodiment. This analysis method includes a sample collecting step S1, a mixing step S2, an electrophoretic liquid filling step S3, an introducing step S4, a removing step S11, and an electrophoresis step S5.

<Sample Collecting Step S1>

First, a sample Sa is prepared. In this embodiment, the sample Sa is blood collected from a human body. The blood may be whole blood, or may be hemolyzed blood subjected to hemolysis treatment, for example. Then, the analysis chip 2 to which the sample Sa was injected is set in the analysis device 1.

<Mixing Step S2>

Figure 5:
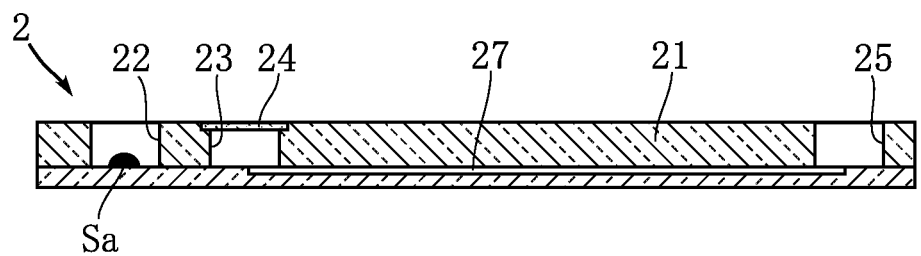
FIG. 5 is a cross-sectional view showing the analysis method in FIG. 4.
Figure 6:
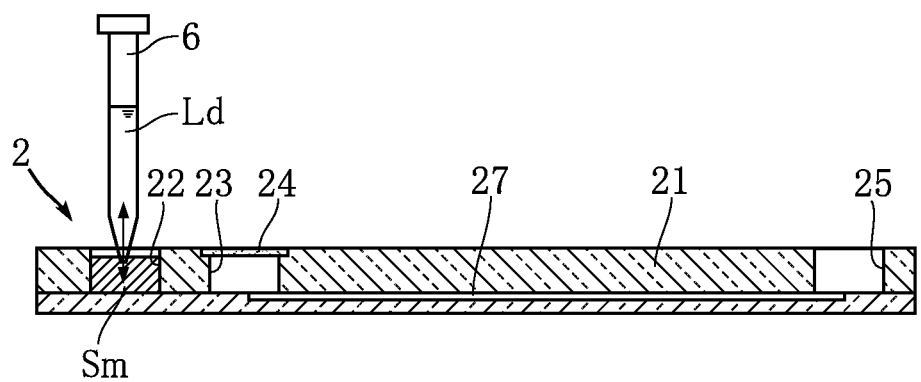
FIG. 6 is a cross-sectional view showing the analysis method in FIG. 4.

Then, the sample Sa and the diluting liquid Ld are mixed. Specifically, as shown in FIG. 5, a predetermined amount of sample Sa has been added dropwise to the mixing tank 22 of the analysis chip 2. Then, a predetermined amount of diluting liquid Ld in the diluting liquid tank 71 is sucked by the injector 6, and, as shown in FIG. 6, the predetermined amount of diluting liquid Ld is injected to the mixing tank 22 of the analysis chip 2. The diluting liquid Ld is repeatedly sucked into and ejected from the injector 6, using the pump 61 as the suction source and the ejection source. Accordingly, the sample Sa and the diluting liquid Ld are mixed in the mixing tank 22, so that a mixed sample Sm is obtained. The sample Sa and the diluting liquid Ld may be mixed using a method other than that performs the suction and ejection into and from the injector 6. With the mixing step S2, a complex in which the analysis component s-HbA1c and chondroitin sulfate are bound to each other is generated.

Experiments and researches by the inventors have shown that, in the mixing step S2, an aggregate of a sub component other than the analysis component, among the components contained in blood that is the sample Sa, and chondroitin sulfate that is an example of the anionic group-containing compound may be formed. It was found that specific examples of the sub component include lipids.

<Electrophoretic Liquid Filling Step S3>

Figure 7:
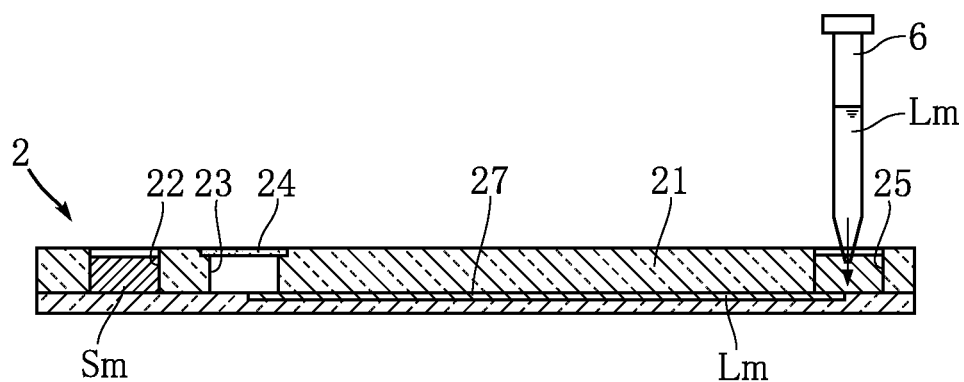
FIG. 7 is a cross-sectional view showing the analysis method in FIG. 4.

Then, a predetermined amount of electrophoretic liquid Lm in the electrophoretic liquid tank 72 is sucked by the injector 6, and, as shown in FIG. 7, the predetermined amount of electrophoretic liquid Lm is injected to the discharging tank 25 of the analysis chip 2. Then, for example, using a method that performs as appropriate suction and ejection through ports as described above, the discharging tank 25 and the capillary tube 27 are filled with the electrophoretic liquid Lm.

<Introducing Step S4 and Removing Step S11>

Figure 8:
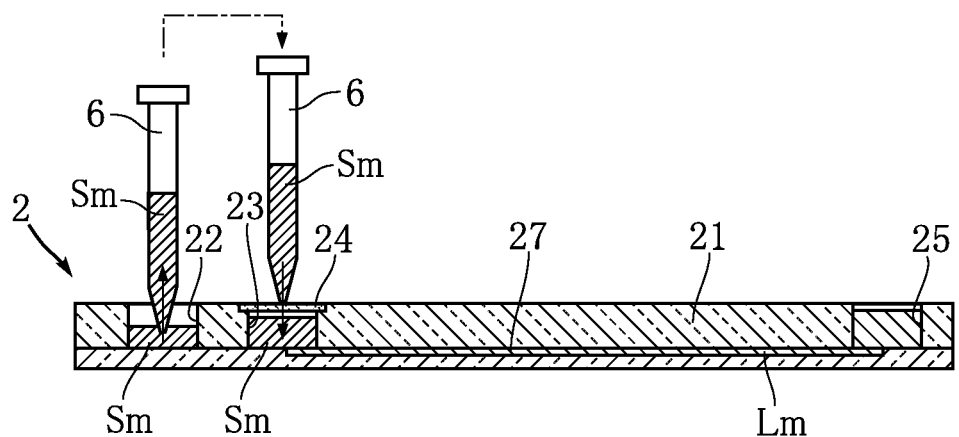
FIG. 8 is a cross-sectional view showing the analysis method in FIG. 4.

Then, as shown in FIG. 8, a predetermined amount of mixed sample Sm is collected from the mixing tank 22 by the injector 6. Then, the predetermined amount of mixed sample Sm is introduced from the injector 6 to the introducing tank 23. In this introduction, the mixed sample Sm passes through the filter 24 provided at the opening portion of the introducing tank 23 (i.e., an example of an introduction path to the introducing tank 23). At that time, an aggregate of the subcomponent (e.g., lipids) and the anionic group-containing compound (chondroitin sulfate, in this embodiment) contained in the mixed sample Sm is removed by the filter 24. This step is the removing step S11. Furthermore, in parallel with the removing step S11, the introducing step S4 of introducing the mixed sample Sm to the introducing tank 23 is performed. Furthermore, in this embodiment, the mixed sample Sm is transmitted from the introducing tank 23 via the communication flow path 28 to fill the electrode tank 26.

<Electrophoresis Step S5>

Then, as shown in FIG. 1, the electrode 31 is inserted into the electrode tank 26, and the electrode 32 is inserted into the discharging tank 25. Subsequently, in response to an instruction from the control portion 8, a voltage is applied to the electrode 31 and the electrode 32. This voltage is, for example, 0.5 kV to 20 kV. Accordingly, an electroosmotic flow is generated, so that the mixed sample Sm is gradually moved through the capillary tube 27 from the introducing tank 23 to the discharging tank 25. At that time, since the introducing tank 23 is filled with the mixed sample Sm, a complex in which the analysis component s-HbA1c and chondroitin sulfate are bound to each other is subjected to electrophoresis in the capillary tube 27 in a state where the mixed sample Sm is continuously supplied. In this state, emission of light from the light source 41 is started, and the light absorbance is measured by the detector 5. Furthermore, a relationship between the period of time elapsed after the start of voltage application from the electrode 31 and the electrode 32 and the light absorbance is measured. A light absorbance peak corresponding to a component having a relatively high migration rate in the mixed sample Sm appears in a relatively short period of time elapsed after the start of voltage application. On the other hand, a light absorbance peak corresponding to a component having a relatively low migration rate in the mixed sample Sm appears in a relatively long period of time elapsed after the start of voltage application. Accordingly, an analysis (measurement by separation) of components in the mixed sample Sm is performed. The measured light absorbance is subjected to arithmetic processing (e.g., differential processing, difference processing, etc. by the control portion 8), so that an electropherogram is obtained. The component ratio and the like in the mixed sample Sm are obtained by calculating a peak height or a peak area of this electropherogram.

Next, examples of this analysis method will be described.

EXAMPLE 1

As the sample Sa, a sample obtained by adding 5 μL of fat emulsion for intravenous use (Intralipos (manufactured by Otsuka Pharmaceutical Co., Ltd.: registered trademark) infusion 20%), for example, as a substitute for lipids that would be contained in blood of a patient with hyperlipidemia, to 95 μL of whole blood collected from a healthy person was used. As the electrophoretic liquid Lm, a liquid prepared using 40 mM citric acid, 1.25% (w/v) chondroitin sulfate C-sodium, 0.1% (w/v) LS-110 (manufactured by Kao Corporation), 0.02% (w/v) sodium azide, and 0.025% (w/v) ProClin950 (manufactured by Sigma-Aldrich: registered trademark) and having a pH adjusted to 5.0 using dimethylaminoethanol (for pH adjustment) was used. As the diluting liquid Ld, a liquid prepared using 40 mM citric acid, 1.0% (w/v) chondroitin sulfate C-sodium, 500 mM NDSB-201 (manufactured by Anatrace), 0.1% (w/v) LS-110 (manufactured by Kao Corporation), 0.02% (w/v) sodium azide, and 0.025% (w/v) ProClin950 (manufactured by Sigma-Aldrich: registered trademark) and having a pH adjusted to 6.0 using dimethylaminoethanol (for pH adjustment) was used.

As the analysis chip 2, an introducing tank 23 having a capacity of 10 μL, a discharging tank 25 having a capacity of 10 μL, and a capillary tube 27 having a width of 40 μm, a depth of 40 μm, and a total length of 30 mm (separation length 20 mm) were prepared. The inner wall of the capillary tube was coated with poly(diallyldimethylammoniumchloride) (PDADMAC: manufactured by Sigma). As the filter 24, a cellulose acetate membrane filter (manufactured by ADVANTEC, pore size 0.45 μm) was used.

In the mixing step S2, the sample Sa was diluted 41 times with the diluting liquid Ld, so that a mixed sample Sm was obtained. The amount of electrophoretic liquid Lm filled in the electrophoretic liquid filling step S3 was 9 μL. In the introducing step S4 and the removing step S11, the mixed sample Sm was introduced in an amount obtained by adding an amount corresponding to the capacities of the electrode tank 26 and the communication flow path 28 to 9 μL. In the electrophoresis step S5, the electrode 31 and the electrode 32 had a voltage of 0.5 kV to 20 kV and a current of 76 μA. With the detector 5, the light absorbance at a wavelength of 415 nm was measured, so that the electropherogram was obtained. The electrophoresis was performed for 30 seconds. This measurement was performed five times, and the simultaneous repeatability was evaluated.

COMPARATIVE EXAMPLE

Measurement was performed as in Example 1, except that the removing step S11 using the filter 24 was not performed. This measurement was performed five times, and the simultaneous repeatability was evaluated.

Figure 9:
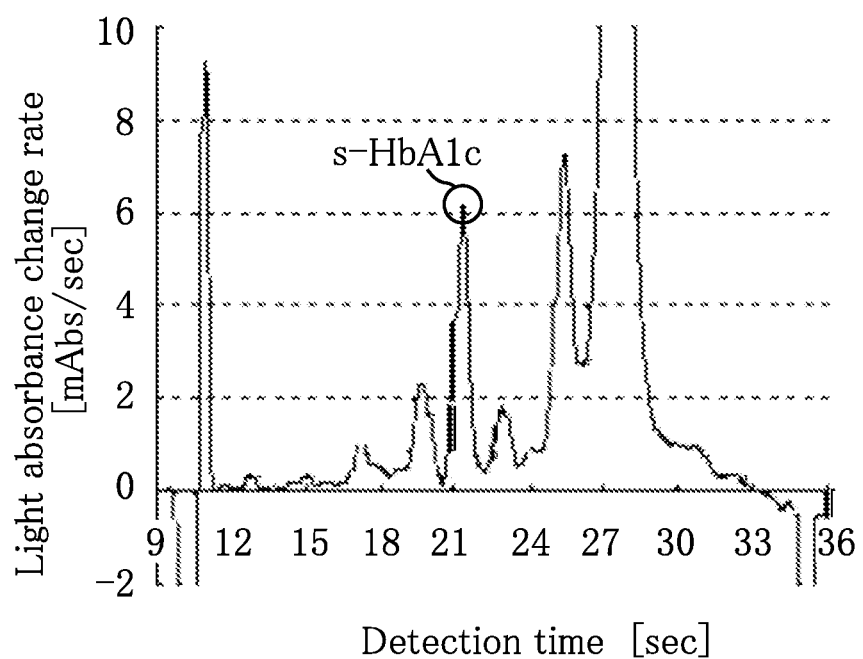
FIG. 9 is an electropherogram showing a result of an example of the analysis method in FIG. 4.
Figure 10:
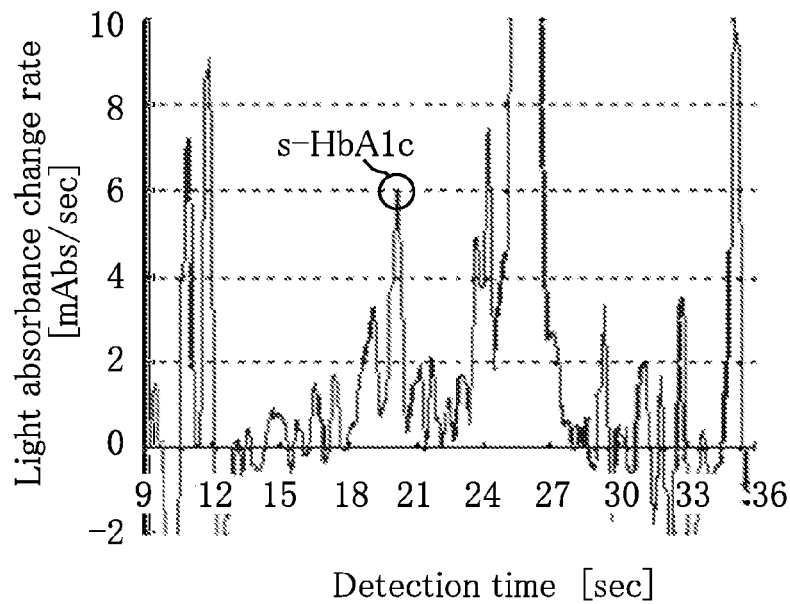
FIG. 10 is an electropherogram showing a result of a reference example of an analysis method.

FIG. 9 shows the electropherogram obtained in Example 1, and FIG. 10 shows the electropherogram obtained in Comparative Example. In these electropherograms, the horizontal axis indicates a detection time (unit: sec), and the vertical axis indicates a light absorbance change rate (unit: mAbs/sec). Furthermore, Table 1 shows evaluation results of the simultaneous repeatability of the s-HbA1c analysis results in Example 1 and Comparative Example. In the table, a numerical value in each measurement indicates the percentage (%) of the hemoglobin s-HbA1C concentration with respect to the total hemoglobin concentration. The peak around 21 to 22 seconds in FIG. 9 and the peak around 20 to 21 seconds in FIG. 10 are light absorbance peaks corresponding to the analysis component s-HbA1c.

TABLE 1

|  | Ex. 1 | Com. Ex. |
| --- | --- | --- |
| Measurement 1 | 5.20 | 5.39 |
| Measurement 2 | 5.26 | 6.77 |
| Measurement 3 | 5.24 | 6.05 |
| Measurement 4 | 5.23 | 5.56 |
| Measurement 5 | 5.20 | 6.43 |

TABLE 1-continued

|  | Ex. 1 | Com. Ex. |
| --- | --- | --- |
| Average | 5.23 | 6.04 |
| Standard deviation | 0.03 | 0.58 |
| CV (%) | 0.50 | 9.58 |

Next, the actions of the analysis system A1 and this analysis method will be described.

As shown in FIGS. 9 and 10, the s-HbA1C light absorbance peak appeared at substantially the same time. The shapes of the electropherogram before and after this s-HbA1C light absorbance peak appeared in Example 1 in FIG. 9 are significantly smoother than those in Comparative Example in FIG. 10. In other words, the electropherogram in FIG. 10 has a shape having a large number of small fluctuations. Furthermore, as shown in Table 1, the standard deviation and the coefficient of variation (CV) in the s-HbA1C analysis result in Example 1 were smaller than those in Comparative Example. Accordingly, it can be assured that Example 1 had a better repeatability than Comparative Example. As a result of research conducted by the inventors, it was found that this difference is caused by the fact that, in Example 1, the mixed sample Sm passed through the filter 24 in the removing step S11, so that an aggregate of the sub component (e.g., lipids) and the anionic group-containing compound (chondroitin sulfate, in this embodiment) contained in the mixed sample Sm had been removed. That is to say, the aggregate was seen in the mixed sample Sm before the removing step S11 was performed, whereas the aggregate was hardly seen in the mixed sample Sm after the removing step S11 was performed. Thus, the inventors concluded that, in electrophoresis, the aggregate appears in an electropherogram as the small fluctuations in FIG. 10, that is, as noise. It seems that, since such an aggregate had been removed, the repeatability in Example 1 was improved. Furthermore, the average values of the measurement results are different between Example 1 and Comparative Example, and the average value in Example 1 seems to be more reliable. Accordingly, the analysis system A1 and this analysis method can improve the analysis precision.

In the electrophoresis step S5 of this analysis method, electrophoresis is performed in a state where the mixed sample Sm is continuously supplied. Accordingly, for example, it is not necessary to draw a predetermined amount of mixed sample Sm that is to be supplied to the capillary tube 27. In an analysis method that draws a predetermined amount of mixed sample Sm, a relatively complicated mechanism for drawing a predetermined amount has to be provided. According to this analysis method and the analysis system A1, it is not necessary to draw a predetermined amount of mixed sample Sm, and, thus, the size of the analysis chip 2 can be made relatively small. This aspect is advantageous when using the analysis chip 2 as a disposable analysis chip.

Since the filter 24 is provided at the opening portion of the introducing tank 23 (i.e., an introduction path to the introducing tank 23), the introducing step S4 and the removing step S11 can be performed in parallel. The filter 24 is provided in the analysis chip 2 that is disposable, and, thus, when one analysis ends, it is disposed of together with the analysis chip 2. Accordingly, the filter 24 used to remove the aggregate is not left in the analysis device 1, and the analysis method can be efficiently and cleanly carried out a plurality of times.

Contrary to the above-described configuration, the filter 24 can be provided as appropriate on the introduction path to the introducing tank 23. For example, in the configuration in which the mixing tank 22 and the introducing tank 23 are linked via a flow path, the filter 24 can be provided at a point on the flow path or at a link portion between the flow path and the mixing tank 22 or the introducing tank 23. When the mixed sample Sm obtained in the mixing tank 22 is introduced from the mixing tank 22 via the flow path to the introducing tank 23, the aggregate is removed by the filter 24.

Although the sub component forming the aggregate seems to be very often a lipid in the case of blood collected from a patient with hyperlipidemia or the like, the specific example of the sub component is not limited to lipids. The sub component may be any component that is a component other than the analysis component contained in the sample Sa such as blood and that will form an aggregate with the anionic group-containing compound.

Figure 11:
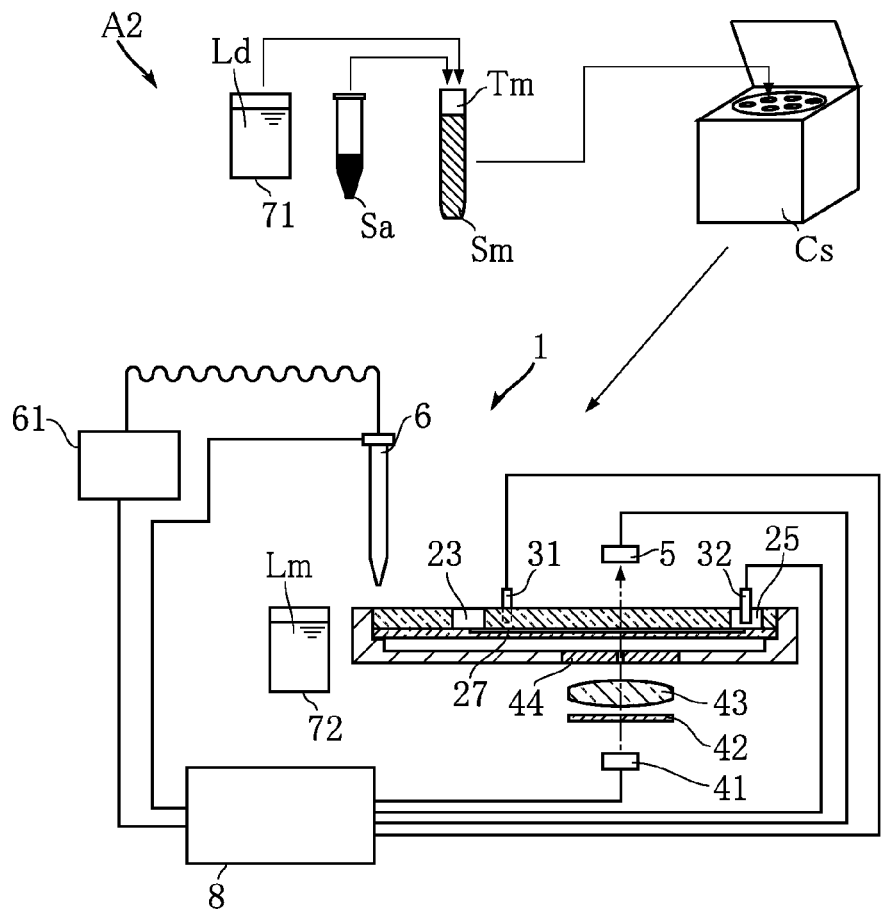
FIG. 11 is a schematic system view showing an analysis system according to a second embodiment of the present invention.
Figure 12:
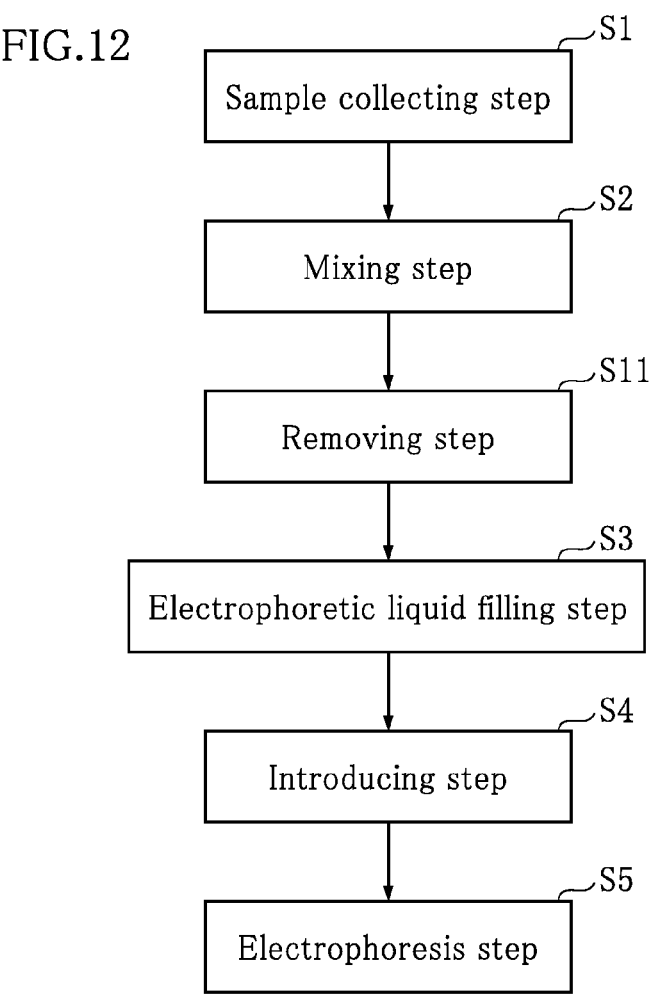
FIG. 12 is a flowchart showing an analysis method according to the second embodiment of the present invention.

FIGS. 11 and 12 show another embodiment of the present invention. In these drawings, the constituent elements that are the same as or similar to those in the foregoing embodiment are denoted by the same reference numerals as in the foregoing embodiment.

FIG. 11 is a schematic system view showing an analysis system according to a second embodiment of the present invention. FIG. 12 is a flowchart showing an analysis method of this embodiment.

As shown in FIG. 11, an analysis system A2 includes the analysis device 1, the analysis chip 2, the diluting liquid tank 71, a mixing tank Tm, and a centrifugal separator Cs.

Contrary to the foregoing embodiment, the analysis device 1 does not include the diluting liquid tank 71 and the filter 24. Except for this aspect, the configuration of the analysis device 1 is the same as that of the analysis device 1 in the analysis system A1 described above.

In this embodiment, the diluting liquid tank 71 for storing the diluting liquid Ld is provided outside the analysis device 1. Also, the mixing tank Tm is provided outside the analysis device 1.

The centrifugal separator Cs is for performing the removing step S11 in the analysis method of this embodiment using the analysis system A2, and is an example of a removing portion (centrifugal separation means) in the present invention. As the centrifugal separator Cs, for example, a device that centrifuges blood is used as appropriate.

As shown in FIG. 12, in the analysis method of this embodiment, the sample collecting step S1, the mixing step S2, the removing step S11, the electrophoretic liquid filling step S3, the introducing step S4, and the electrophoresis step S5 are performed in this order.

After the sample Sa shown in FIG. 11 is collected, the sample Sa and a predetermined amount of diluting liquid Ld from the diluting liquid tank 71 are injected to the mixing tank Tm. In the mixing tank Tm, the mixing step S2 of mixing the sample Sa and the diluting liquid Ld is performed. Accordingly, the mixed sample Sm is obtained. Then, in a state where a predetermined amount of mixed sample Sm is collected in a predetermined container or is kept stored in the mixing tank Tm, the mixed sample Sm is set in the centrifugal separator Cs. With the centrifugal separation by the centrifugal separator Cs, an aggregate of the sub component (lipids) and the anionic group-containing compound (chondroitin sulfate) in the mixed sample Sm settles at the bottom (the removing step S11). Subsequently, a predetermined amount of mixed sample Sm is collected from a region spaced away from the aggregate settlement region toward the liquid surface of the mixed sample Sm, and is introduced to the introducing tank 23 of the analysis chip 2 (the introducing step S4). Also, the electrophoretic liquid filling step S3 is performed. Subsequently, the electrophoresis step S5 as described above is performed.

EXAMPLE 2

Figure 13:
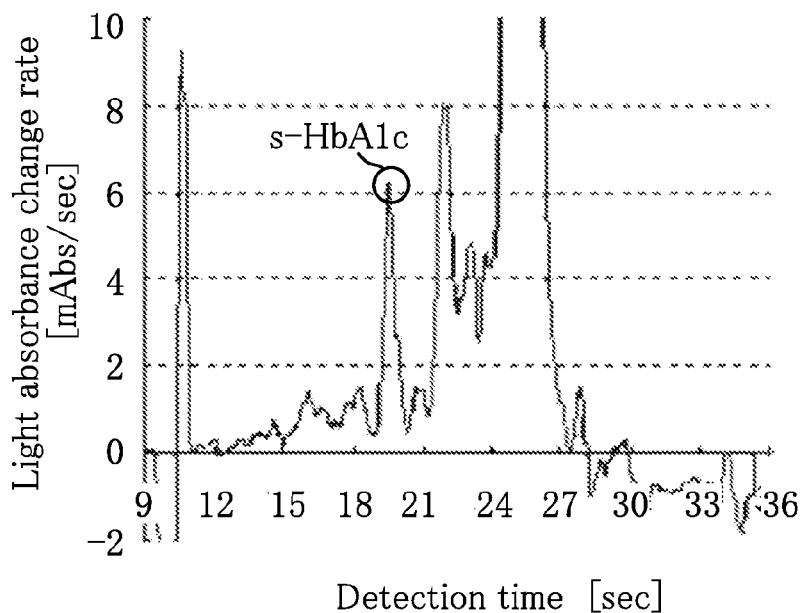
FIG. 13 is an electropherogram showing a result of the analysis method in FIG. 12.

Hereinafter, an example of the embodiment using the analysis system A2 (referred to as Example 2, for the sake of convenience) will be described. In this example, in the removing step S11, the mixed sample Sm was centrifuged using the centrifugal separator Cs at 8000 G for 10 minutes. The other conditions were the same as those in Example 1 and Comparative Example described above. FIG. 13 shows the electropherogram obtained in Example 2. Furthermore, Table 2 shows evaluation results of the simultaneous repeatability of the s-HbA1c analysis results in Example 2 and Comparative Example described above.

TABLE 2

|  | Ex. 2 | Com. Ex. |
|---|---|---|
| Measurement 1 | 5.30 | 5.39 |
| Measurement 2 | 5.22 | 6.77 |
| Measurement 3 | 5.39 | 6.05 |
| Measurement 4 | 5.39 | 5.56 |
| Measurement 5 | 5.30 | 6.43 |
| Average | 5.32 | 6.04 |
| Standard deviation | 0.07 | 0.58 |
| CV (%) | 1.35 | 9.58 |

Comparison between the electropherogram in Example 2 in FIG. 13 and the electropherogram in Comparative Example in FIG. 10 shows that noise considered to be resulting from an aggregate was significantly small in the electropherogram in Example 2, as in the case of the electropherogram in Example 1. Furthermore, as shown in Table 2, the standard deviation and the CV in Example 2 were smaller than those in Comparative Example, and, thus, it can be assured that Example 2 had an excellent repeatability. Note that, compared with Comparative Example, Examples 1 and 2 had average values that were close to each other, and standard deviations and CVs that were small.

The analysis method and the analysis system according to the present invention are not limited to the foregoing embodiments. The specific configuration of each portion in the analysis method and the analysis system according to the present invention can be variously designed and modified.

The filtering means is not limited to the filter 24 provided inside the analysis chip 2. For example, a configuration is possible in which, instead of the centrifugal separator Cs in the analysis system A2, a filtering means including a predetermined filter is provided outside the analysis device 1. Furthermore, the filtering means and the centrifugal separation means are merely examples of the removing portion in the present invention, and various mechanisms may be used as long as undesired substances such as aggregates that may cause noise in results such as electropherograms in the above-described electrophoresis method.

The invention claimed is:

1. A system for analyzing a sample using a capillary electrophoresis method, the system comprising:
   a disposable analysis chip comprising a capillary tube, an introducing tank linked to one end of the capillary tube, and a discharging tank linked to the other end of the capillary tube;
   an original sample containing an analysis component to be analyzed and a subcomponent other than the analysis component;
   a removing portion that removes an aggregate of the subcomponent and an anionic group-containing compound from a mixed sample that is formed by mixing the original sample and the anionic group-containing compound, wherein the removing portion comprises a filter that is provided at a point in an introduction path to the introducing tank;
   an injector that fills an electrophoretic liquid to the capillary tube such that the electrophoretic liquid does not contact the filter; and
   an analysis portion that performs electrophoresis in the capillary tube with a complex in which the analysis component and the anionic group-containing compound are bound to each other, in a state where the mixed sample is continuously supplied,
   wherein the mixed sample, in which the aggregate has been removed, is introduced to the introducing tank.

2. The system according to claim 1, wherein the removing portion has a centrifugal separator.

3. The system according to claim 2, wherein the centrifugal separator is provided so as to perform a centrifugal separation of the mixed sample to separate the aggregate before performing electrophoresis.

4. The system according to claim 2, wherein the centrifugal separator is provided upstream of the analysis portion in a sample analysis flow.

5. The system according to claim 2, wherein the system comprises a mixing portion in which the original sample and the anionic group-containing compound are mixed.

6. The system according to claim 1, wherein the filter is provided upstream of the introducing tank and the capillary tube.

7. The system according to claim 1, wherein the filter removes the aggregate of the subcomponent and the anionic group-containing compound from the mixed sample that is obtained by mixing the original sample and the anionic group-containing compound before the mixed sample is introduced to the capillary tube.

8. The system according to claim 1, wherein the filter is a cellulose acetate membrane filter.

9. The system according to claim 1, wherein the filter has a pore size of about 0.45 μm.

10. The system according to claim 6, wherein the filter is provided at an opening portion of the introducing tank.

11. The system according to claim 6, wherein the chip comprises a mixing portion in which the original sample and the anionic group-containing compound are mixed.

12. The system according to claim 11, wherein the mixing portion and the introducing tank are linked via a flow path.

13. The system according to claim 6, wherein the chip comprises an electrode tank into which an electrode is inserted.

14. The system according to claim 1, wherein the filter is provided upstream of the introducing tank and the capillary tube and downstream of the mixing tank.

15. A system for analyzing a sample using a capillary electrophoresis method, the system comprising:
   a capillary tube;
   a mixing tank to mix a sample and a diluting liquid;
   an introducing tank that is linked to one end of the capillary tube;
   a discharging tank that is linked to the other end of the capillary tube;

a filter that filtrates the mixed sample, wherein the filter is provided at a point in an introduction path to the introducing tank, and the filtrated mixed sample is introduced to the introducing tank;

an injector that fills an electrophoretic liquid to the capillary tube such that the electrophoretic liquid does not contact the filter; and an analysis portion that performs electrophoresis in the capillary tube in a state in which the mixed sample is continuously supplied.

16. The system according to claim 15, wherein the system comprises an analysis chip comprising the capillary tube, the introducing tank, and the discharging tank.

17. The system according to claim 15, wherein the filter is provided upstream of the introducing tank and the capillary tube and downstream of the mixing tank.

* * * * *